United States Patent
Lowe

(10) Patent No.: US 7,328,815 B2
(45) Date of Patent: Feb. 12, 2008

(54) LIQUID BEVERAGE CONDUCTIVITY DETECTING SYSTEM

(75) Inventor: Kevin G. Lowe, Virden, IL (US)

(73) Assignee: Bunn-O-Matic Corporation, Springfield, IL (US)

( * ) Notice: Subject to any disclaimer, the term of this patent is extended or adjusted under 35 U.S.C. 154(b) by 0 days.

(21) Appl. No.: 10/524,707

(22) PCT Filed: Aug. 13, 2003

(86) PCT No.: PCT/US03/25292

§ 371 (c)(1),
(2), (4) Date: Mar. 10, 2006

(87) PCT Pub. No.: WO2004/014781

PCT Pub. Date: Feb. 19, 2004

(65) Prior Publication Data

US 2006/0191954 A1  Aug. 31, 2006

(51) Int. Cl.
*B67D 5/08* (2006.01)

(52) U.S. Cl. .............. 222/52; 222/1; 222/54; 222/56; 222/64; 222/129.1; 222/129.2; 222/145.5; 222/145.6

(58) Field of Classification Search .......... 222/1, 222/129–129.4, 145.5, 459, 145.6, 145.7, 222/64, 145.8, 54, 161–163, 145.1, 52; 99/323.2, 99/323.3; 366/165.3, 165.1, 165.2
See application file for complete search history.

(56) References Cited

U.S. PATENT DOCUMENTS

| | | | |
|---|---|---|---|
| 6,202,894 B1 * | 3/2001 | Struminski et al. ...... 222/129.3 |
| 6,240,829 B1 | 6/2001 | McGarrah | |
| 6,349,852 B1 | 2/2002 | Ford | |
| 6,387,424 B2 | 5/2002 | Funk | |
| 6,419,120 B1 * | 7/2002 | Bertone ............... 222/129.4 |
| 6,446,835 B1 | 9/2002 | Ford | |
| 7,036,687 B1 * | 5/2006 | Lowe ................ 222/145.5 |

OTHER PUBLICATIONS

International Search Report, date of completion Jan. 20, 2004, for PCT/US2003/25292.

* cited by examiner

*Primary Examiner*—Frederick C. Nicolas
(74) *Attorney, Agent, or Firm*—Barnes & Thornburg LLP

(57) ABSTRACT

The present disclosure relates to a system, method and apparatus for controlling the flavor of a beverage produced from a concentrate, based on the conductivity of the beverage being produced. The apparatus includes a conductivity sensor which provides a controller with real time conductivity data from the beverage being served. The controller is capable of comparing the real time conductivity data to a preprogrammed range of conductivity readings and adjusting a variable speed pump to keep the real time conductivity data within the preprogrammed range.

6 Claims, 3 Drawing Sheets

LIQUID BEVERAGE CONDUCTIVITY DETECTING SYSTEM

BACKGROUND

The present disclosure contemplates a method, system and apparatus for producing and dispensing food products such as beverages made from a concentrate.

There are numerous beverage preparation systems that use a concentrate substance to prepare a beverage. Typically, the beverage concentrate is diluted with another substance, such as water, to prepare the desired resultant beverage, for example coffee, tea or juice to name a few. The concentrate may be in the form of a frozen, chilled, room temperature or heated prepackaged liquid or may also be a freshly brewed or otherwise prepared concentrate liquid. Additionally, powdered, gel, gaseous, granulated or other concentrates may be used.

The concentrate may be contained in a variety of containers. For example, one form of packaged beverage concentrates come in a "bag-in-box" arrangement where a plastic bag containing the beverage concentrate is contained within a box. Other containers such as metallic cylinders or plastic bottles may be used. The "bag-in-box" containing the desired concentrate is attached to a dispensing apparatus. Heated water in the case of coffee or tea, or chilled or room temperature water in the case of juice is then combined with a predetermined volume of concentrate to yield a resulting beverage with desired flavor characteristics. The proper volume of diluting water and concentrate are typically measured as a factor of time. For example, for a unit of beverage to be produced, a pump dispensing a concentrate must operate for a preselected period of time to deliver a predetermined volume of concentrate. At the same time, a valve must be opened for a preselected period of time to deliver a predetermined volume of diluting water. The combination of the pump and valve operating for preselected periods of time will produce a beverage with a desired flavor characteristic.

The concentrate and diluting water may be alternatively introduced at separate times into a container from which the resulting beverage is dispensed or consumed. Another possibility is to combine the concentrate and diluting water in a mixing chamber prior to dispensing into a container.

One difficulty with measuring the amount of concentrate used as a function of time is the inability of the beverage preparation system to adjust to conditions such as non-uniform concentration of the concentrate, differences in concentrate viscosity, or temperature differences which may cause a concentrate to flow from a container at varying rates. In such instances, a beverage preparation system that utilizes time to measure the proper amount of concentrate to be dispensed will produce beverages with varying amounts of concentrate and thus varying flavors that may fall outside a desired range for the resulting beverage.

It is expected that there are other beverage dispensing and diluting systems which will benefit from the present disclosure which provides improved accuracy, consistency, repeatability and uniformity in the mixing and dispensing of beverages formed from a concentrate.

The present disclosure relates to a method, system and apparatus for producing and dispensing beverages made from a concentrate. An object of the present disclosure is a conductivity detecting system, which monitors the conductivity of a diluted beverage during the mixing and dispensing process and works in combination with a controller to adjust the volume of concentrate dispensed, thereby consistently producing a more uniform beverage.

The present disclosure provides a mixing chamber and a method of introducing concentrate and diluting water into the mixing chamber which will give rise to more accurate detection of conductivity of the resulting beverage within the mixing chamber.

Briefly, a method, system and apparatus for producing and dispensing beverages made from a concentrate is disclosed. A conductivity detecting system is provided within a mixing chamber for measuring the conductivity of a beverage therein. The conductivity sensor works in combination with a controller, a concentrate pump and a controllable valve to adjust the volume of concentrate dispensed into the mixing chamber thereby keeping the resulting beverage conductivity within a specified range which defines the desired flavor for the particular beverage being produced.

The present disclosure also contemplates a system for dispensing concentrated beverages with a desired flavor. The desired flavor is expressed in terms of a conductivity measurement which is then input into a controller. The controller then regulates and adjusts the flow of concentrate into a mixing chamber based on conductivity readings provided by conductivity sensors in order to produce a beverage having the desired conductivity value.

Additional features will become apparent to those skilled in the art upon consideration of the following detailed description of drawings, illustrative of at least one embodiment of the disclosure.

BRIEF DESCRIPTION OF THE DRAWINGS

The detailed description refers to the accompanying figures in which.

DETAILED DESCRIPTION OF THE DRAWINGS

Figure 1:
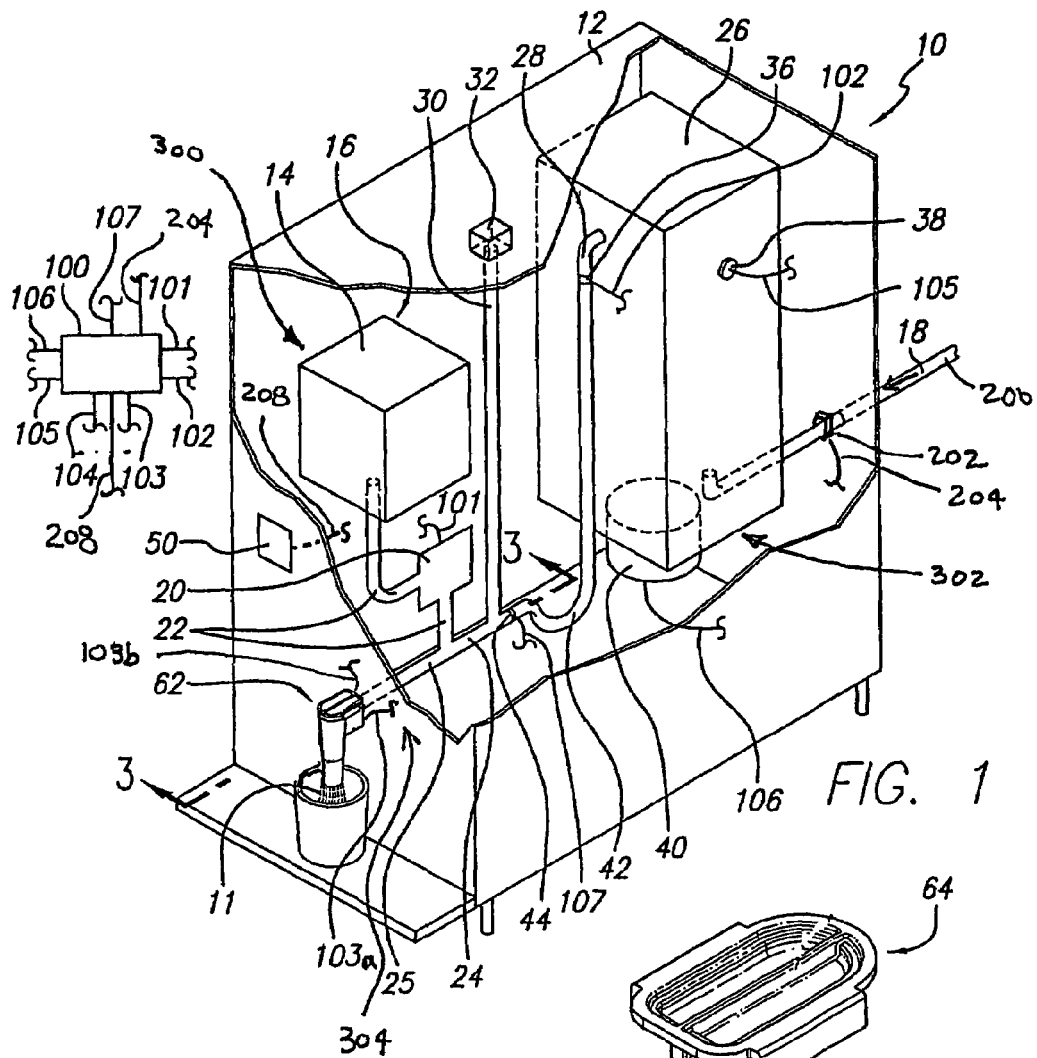
FIG. 1 is a diagrammatic perspective view of a beverage dispensing system with a conductivity detecting system.

While the present invention may be susceptible various modifications and alternative forms, there is shown in the drawings, and herein will be described in detail, embodiments with the understanding that the present description is to be considered an exemplification of the principles of the disclosure and is not intended to limit the disclosure to the details of construction and the arrangements of components set forth in the following description or illustrated in the drawings. The intention of this disclosure is to cover all modifications, equivalents, and alternatives falling within the spirit and scope of the invention as defined by the appended claims.

U.S. Pat. No. 6,387,424 issued to Robert C. Funk on May 14, 2002 and assigned to the assignee of the present application is expressly incorporated herein by reference.

Terms including brewed, brewing, brewing substance, brewing liquid, beverage, and brewed beverage as used herein are intended to be broadly defined as including but not limited to the brewing of coffee, tea and any other brewed beverage. This broad interpretation is also intended to include, but is not limited to any process of infusing, steeping, reconstituting, diluting, dissolving, saturating or passing a liquid through or otherwise mixing or combining a beverage substance with a liquid such as water without a limitation to the temperature of such liquid unless specified. This broad interpretation is also intended to include, but is not limited to beverage substances such as ground coffee, tea, liquid beverage concentrate, powdered beverage concentrate, freeze dried coffee or other beverage concentrates, to obtain a desired beverage or other food.

With reference to the figures, a beverage dispensing system 10 is shown in FIG. 1. This system generally produces a beverage 11 by combining a beverage concentrate 14 with a dilution material such as diluting water 18. A housing 12 having a generally rectangular shape is diagramatically shown in FIG. 1. The housing 12 contains a number of components which form the beverage dispensing system 10. The housing 12 also makes the beverage dispensing system 10 more sanitary and user friendly by allowing a user access to only a serving spout 62 and a control panel 50. It is contemplated that any number of geometric shapes may serve the same function as the rectangular shaped housing 12 shown in FIG. 1. With reference to the diagrammatic illustrations as shown in FIG. 1 it is intended that the present disclosure and invention set forth in the claims is not to be limited by these illustrations. Rather the illustrations are provided in a diagrammatic form so as to incorporate all variations on such diagrammatic forms.

Turning to the components of the beverage dispensing system 10, the beverage concentrate 14 is contained within a container 16. The beverage concentrate 14 may be a concentrated coffee, tea, juice or other beverage and may come in liquid, powder, gel, gaseous, granular, or other form. In one embodiment, the beverage concentrate 14 is a coffee concentrate contained in a "bag-in-box" container. It is contemplated that other suitable containers known to those of skill in the art may be used to provide a beverage concentrate 14. While a bag-in-box container is described, additional containers such as refillable and replaceable containers, other disposable containers or connections to other concentrate supplying devices which are known in the art could be employed. Additionally, a freshly brewed beverage concentrate 14 may be provided for use in the beverage dispensing system 10 of the present disclosure. A system for providing brewed beverage concentrate could be in the form such as the Omni Beverage System manufactured by Bunn-O-Matic Corporation, assignee of the present application, and marketed by Procter and Gamble Corporation of Cincinnati, Ohio. All information relating to the Omni Beverage System is incorporated herein by reference.

The container 16 is connected by a concentrate tube 22 to a pump 20 which is controlled by a controller 100 over a line 101. It is contemplated in one embodiment that the pump 20 is a variable speed pump. An example of a pump which might be employed in the present system is shown in U.S. Pat. No. 6,419,466 issued to Kevin Lowe and Robert Funk on Jul. 16, 2002 and assigned to the assignee of the present application, which patent is expressly incorporated herein by reference. In response to a signal from controller 100, pump 20 operates, causing a controllable variable volume of beverage concentrate 14 to be introduced into an inlet tube 24 where the beverage concentrate 14 comes into contact with diluting water 18. The use of a pump 20 in this system provides a controllable concentrate dispenser. The components including the container 16, pump 20 and tube 22 with the pump 20 being connected to the controller 100 comprise one form of means for delivering concentrate 300 or a controllable concentrate dispensing assembly.

It is envisioned that the pump and concentrate could be positioned external to the housing 12. Furthermore, the pump may take a variety of forms such as peristaltic pump, piston pump, pressurized cylinder pump as well as any other form of pump which might help deliver concentrate to the system. Additionally, it is envisioned that the concentrate 14 could be delivered by gravity through the concentrate tube 22. Instead of a pump 20 a controllable valve may be provided to controllably open and close to deliver a metered amount of concentrate from the concentrate source or container 16 to the system.

While a controller 100 is shown in FIG. 1 generally external to the housing it is envisioned that the controller 100 may be incorporated into the housing to provide a self contained system. In this regard, the lines indicated to be running or otherwise connecting components of the system to the controller 100 are shown in broken form in the interest of clarity. It will be understood by one of skill in the art that a controller of known construction can be provided to controllably operate a variety of components of the system to coordinate and synchronize operation of the system to achieve the desired methods and functions disclosed herein. A variety of forms of such controller 100 expect to be within the skill of one of ordinary skill in the art employing micro processing systems and circuits as well as memory systems and circuits. The memory components providing the ability to program and store desired functionality and control of the various components. The controller 100 has been shown external to the housing 12 in the interest of clarity.

In one embodiment, the diluting water 18 is heated in a reservoir 26 to a predetermined temperature. The temperature is regulated by a thermostat 38, which is coupled over a line 105 to a controller 100. In response to signals from thermostat 38, a heating element 40 is activated and deactivated by controller 100 over a line 106 to maintain the diluting water 18 at a predetermined temperature. This embodiment would be useful in an application to produce heated beverages, such as coffee, tea or hot chocolate. A variety of beverage dispensing systems which use a heated water system provided by Bunn-O-Matic Corporation, Springfield, Ill., all such systems being incorporated herein by reference. For example, such as the Bunn-O-Matic FMD powdered beverage producing systems provide an example of a dispensing system which incorporates concentrate and heated water in which the concentrate is reconstituted by mixing with heated water to produce a desired beverage.

With reference to FIG. 1, incoming water 18 is generally provided to the reservoir 26 through water line 200. Controllable inlet valve 202 is coupled to the controller over line 204. In response to a signal from controller 100, the inlet valve 202 is opened to admit water 18 through line 200. Generally, the water in line 200 is under normal line pressure and is introduced to the reservoir 26 under such line pressure.

Reservoir 26 is connected to an inlet tube 24 by a water tube 28. Diluting water 18 from the reservoir 26 is introduced into water tube 28 through a controllable valve 36. Controllable valve 36 is coupled to controller 100 over a line 102. In response to a signal from controller 100 over line 102, controllable valve 36 opens and causes diluting water 18 to fill water tube 28. Water will not flow from the reservoir 26 even when the inlet valve 202 is open until the valve 36 is open. Once the valve 36 is open, water will flow into the reservoir from line 200 under line pressure and will generally exit the reservoir 26 under approximately the same pressure. The incoming water 18 is introduced toward the bottom of the reservoir 26 so as to position the unheated water close to the heating device or element 40 for more rapid heating. Water in the upper portion of the reservoir 26 is generally at a higher temperature and therefore used during the reconstituting process.

The outflow of diluting water 18 from water tube 28 into inlet tube 24 is regulated by a controllable flow restrictor 44 of known construction. Flow restrictor 44 is coupled to controller 100 over a line 107. In response to signals from controller 100 over line 107, flow restrictor 44 may reduce or increase the flow of diluting water 18 into inlet tube 24. For example, a flow rate of 2.5 ounces per second may be achieved when the flow restrictor 44 fully open. This flow rate may then be reduced to 1.8 ounces per second when the flow restrictor 44 is restricting the fluid flow into inlet tube 24. Thus, controllable valve 36 and flow restrictor 44 work in cooperation with one another to regulate the flow of diluting water 18 in a downstream 25 direction towards concentrate tube 22.

Alternatively, the flow restrictor 44 can be provided in a non-controllable form such as a sleeve which is inserted into inlet tube 24. The internal diameter of inlet tube 24 being generally equal to the external diameter of the flow restrictor 44. The flow restrictor 44 in this configuration, has an inner diameter which is smaller than the internal diameter of the inlet tube 24, resulting in a restriction of the flow in the inlet tube 24.

The components and systems used to deliver dilution material, herein described as diluting water, comprise one form of means for delivering dilution material 302 or a controllable dilution material dispensing assembly. In the embodiment shown and described herein the means 302 include the reservoir 26, inlet line 200, valves 202, 36, lines 28, 42 and any other components to deliver water for mixing with the concentrate.

It is contemplated that other beverages 11 may be produced by beverage dispensing system 10 which require different temperature ranges. For example, a variety of juices may be produced from a beverage concentrate 14. In such an application, diluting water 18 could be introduced into water tube 28 through controllable valve 36 and flow restrictor 44 either chilled or at ambient temperature. In this embodiment, the reservoir 26 may be used as a way of providing an accumulation reservoir for chilling or maintaining a quantity of ambient temperature water. Alternatively, the water may flow through a chilling coil without accumulation in a reservoir or may flow directly to the inlet tube 24 as in the form of an ambient temperature system. Similarly, the concentrate could be chilled or at ambient temperature.

Figure 3:
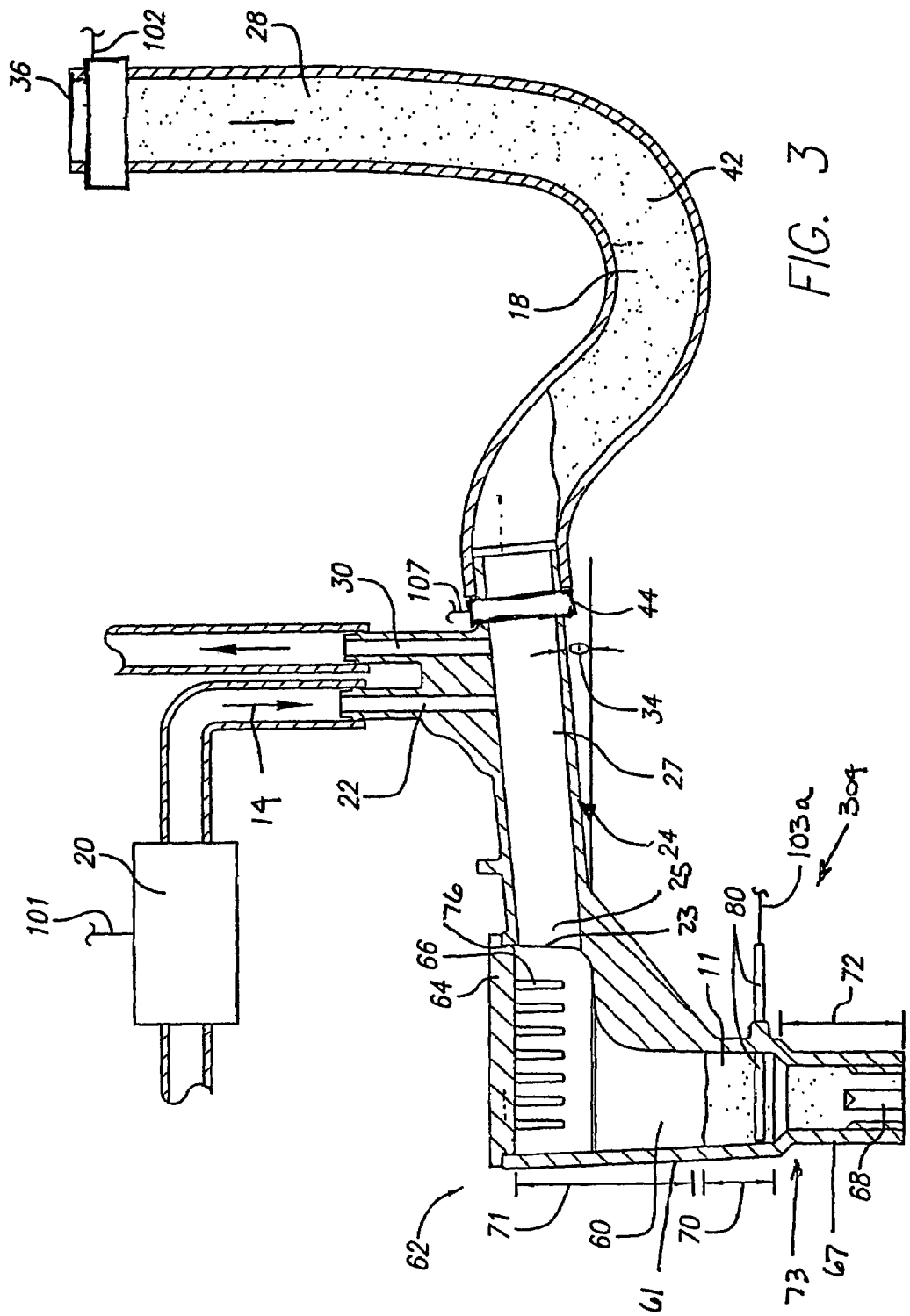
FIG. 3 is an enlarged side elevational view of the serving spout of the beverage dispensing system taken along line 3-3 in FIG. 1.

With reference to FIG. 3, beverage concentrate 14 and diluting water 18 first come into contact with one another at a location where concentrate tube 22 is connected to inlet tube 24. As beverage concentrate 14 and diluting water 18 begin to mix with one another in an upper portion 27 of inlet tube 24 they both continue to flow downstream 25 towards the end 23 of inlet tube 24 at serving spout 62.

The downstream 25 flow of fluid within inlet tube 24 towards serving spout 62 is promoted by angle theta 34. As shown in FIG. 3, inlet tube 24 is mounted or otherwise retained within housing 12 in such orientation that angle theta 34 is formed as an acute angle from a horizontal plane. Angle theta 34 causes or otherwise promotes fluid within inlet tube 24 to run from flow restrictor 44 towards serving spout 62 by gravity. The angle 34 also promote draining or drip out of any liquid in the tube 24 and into the serving spout 62 to help clear liquid and prevent accumulation of liquid or concentrate therein.

To prevent backflow of the diluting water 18 and beverage concentrate 14 contained within inlet tube 24, a P-trap 42 is provided. In addition to preventing backflow, the P-trap 42 also improves the overall sanitation of the beverage dispensing system.

Proximate to concentrate tube 22 is vent tube 30. Vent tube 30 is connected to inlet tube 24 and provides a form of pressure regulation between the interior of inlet tube 24 and the atmosphere. Vent tube 30 also provides for a release of a vacuum which may occur within the interior of inlet tube 24 when controllable valve 36 is in the closed position. The ability to release a vacuum from the interior of inlet tube 24 allows beverage 11 to drain from the beverage dispensing system 10. Vent tube 30 may terminate at a surface of housing 12 under a cover 32. Cover 32 allows for air exchange between the atmosphere and the interior of vent tube 30 while at least partially covering the terminal portion of outlet tube 30 so as to keep the liquid passing though vent tube 24 free of external debris and maintain a sanitary condition. The vent tube 30 may terminate inside the housing 12 as well. Generally, the housing 12 should not form an airtight seal if the vent tube 30 terminates within the housing 12 so as to generally allow the vent tube 30 to equalize to ambient pressure.

Figure 2:
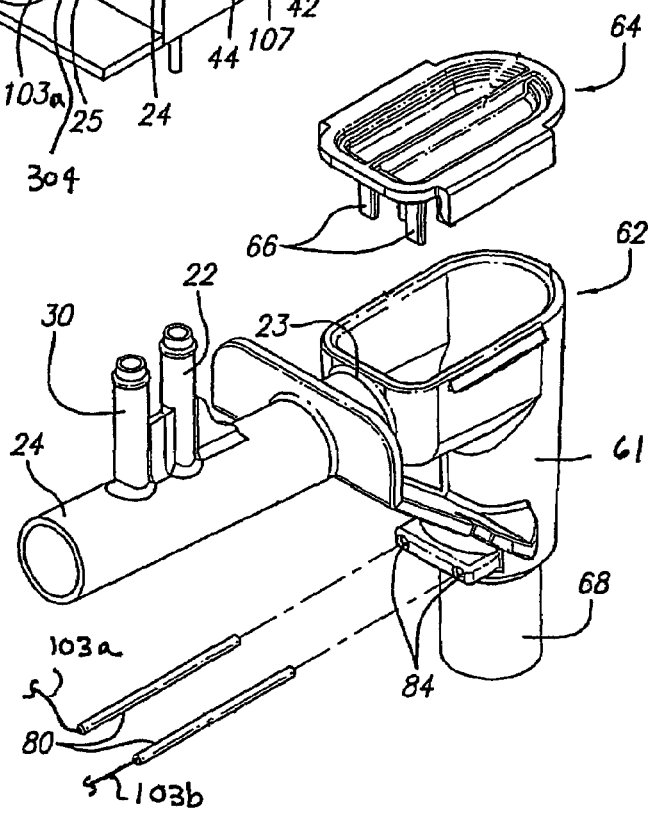
FIG. 2 is an enlarged perspective view of a portion of the beverage dispensing system of FIG. 1 showing a serving spout, supply lines and a pair of conductivity detecting probes.

As seen in FIGS. 2 and 3, serving spout 62 is an outlet from where a user obtains a beverage 11. The serving spout 62 includes a body portion 61 defining a mixing chamber 60 in an upper portion, a removable cover 64 containing a plurality of protrusions 66 is provided and attached to a mouth 76 defined by the body 61 and a laminating structure 68 is provided in a portion of the body 61 defining a nozzle 67 for producing a generally even columnar flow of beverage from the serving spout 62.

An upper portion 71 of the mixing chamber 60 is generally defined by or otherwise limited by the removable cover 64 while a lower portion 70 of the mixing chamber 60 is defined by or otherwise limited by a flow control portion 73 which is defined by a decrease in diameter or size of the mixing chamber 60. This decreased diameter or size results in an area of decreased diameter 72 which restricts or otherwise controls the flow of beverage 11 out of the mixing chamber 60. As a consequence, beverage 11 generally will tend to pool slightly in the lower portion 70 of mixing chamber 60 just above the flow control portion 73 of decreased diameter 72 and tend to form a small collection or pool of beverage 11.

The laminating structure 68 is located below the lower portion 70 of mixing chamber 60 within the nozzle 67 of decreased diameter or size 72. Laminating structure 68 is positioned for directing the resulting beverage 11 downwardly out of serving spout 62 in a generally columnar form by preventing the flow from becoming diffuse, thereby reducing undesired splashing or splattering of the beverage 11.

Turning now to the control aspects of the present disclosure, beverages 11 dispensed by the beverage dispensing system 10 can be characterized by a desired flavor range, flavor profile, or other defining characteristics. The flavor range for each beverage 11 is expressed in the present system 10 in the controller 100 as a conductivity measurement. Each beverage 11 dispensed by the beverage dispensing system 10 is defined in terms of a conductivity measurement which is stored in the controller 100. It is also contemplated that a plurality of conductivity measurements maybe input into the controller 100 for the same type of beverage. For example with coffee, a strong flavor and a mild flavor may be input into the controller 100 as two distinct conductivity measurements. The beverage dispensing system 10 may then be preprogrammed to dispense coffee with one of the two possible flavors from the same beverage concentrate 14. Further, the flavor may be selectable by a user from the control panel 50. The control panel 50 is generally of known construction and is coupled to the controller 100 over line 208.

As seen in FIG. 3, two conductivity probes 80 are provided in the lower portion 70 of the interior of mixing chamber 60. The conductivity probes 80 are positioned in the lower portion 70 because the mixing chamber 60 is designed with a decreased diameter or size to cause a pooling of beverage 11 in the lower portion 70. When a beverage 11 pools in the lower portion 70, the beverage 11 in the pool may be measured by the conductivity probes 80 more accurately than a beverage which only comes into contact with the conductivity probes 80 momentarily as it flows past. The pooling also causes the probes 80 to be fully immersed in and surrounded by mixed beverage to provide a more accurate reading. This pooling of beverage 11 also ensures that more accurate readings are possible by conductivity probes 80 by reducing the probability that air bubbles may form proximate to the conductivity probes 80 and interfere with or create inaccurate readings. Therefore, placing the conductivity probes 80 in a location where a beverage 11 pools will yield a more accurate reading of the conductivity of the beverage 11 being produced by beverage dispensing system 10.

Figure 4:
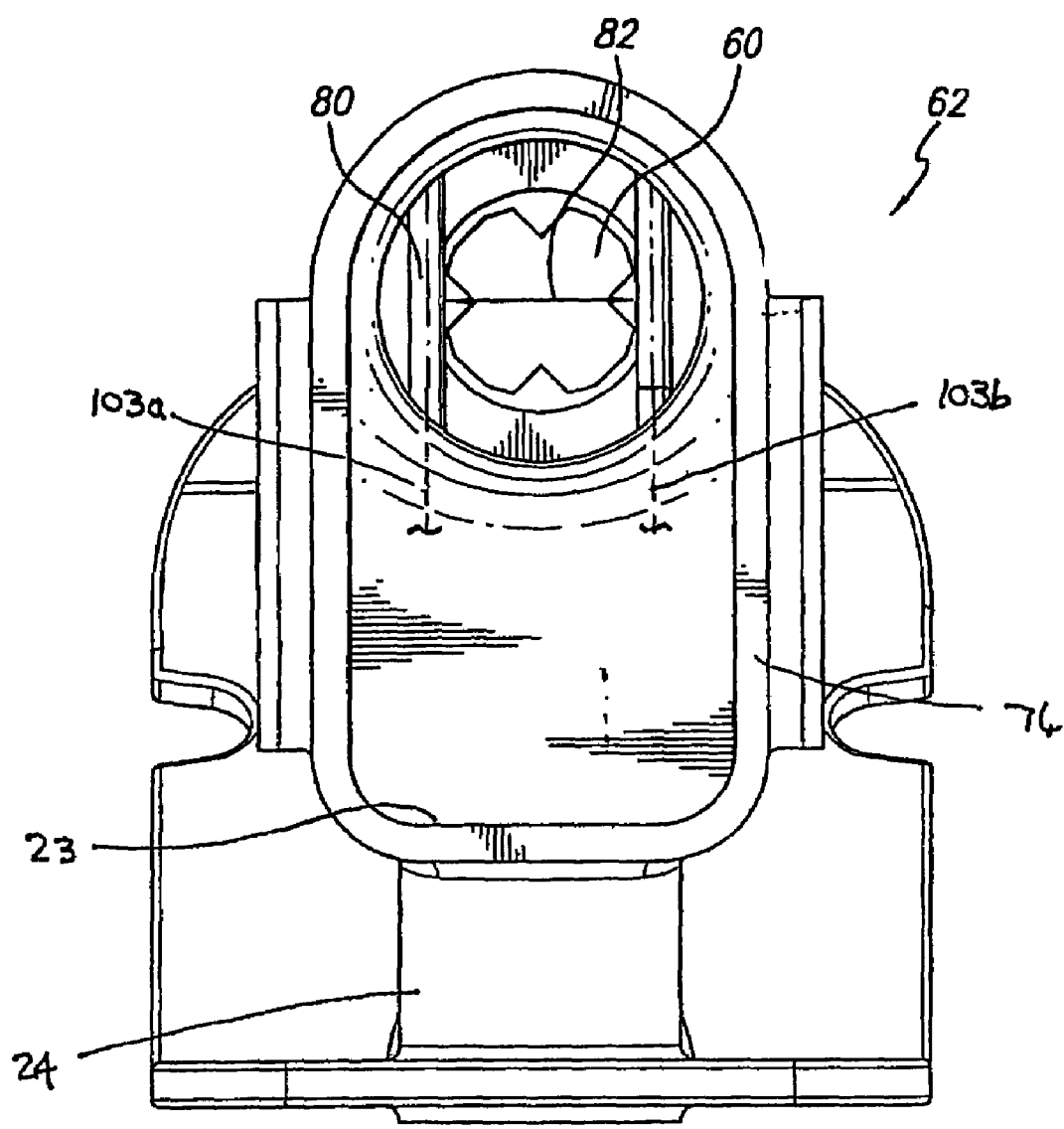
FIG. 4 is a plan view from above an outlet aperture of the serving spout and from which a cover has been removed showing the pair of conductivity probes.

A variety of orientations of the conductivity probes 80 are contemplated by the present disclosure. As shown in FIG. 4, one embodiment contemplates that the conductivity probes 80 are oriented in generally parallel alignment with each other in substantially the same plane and are spaced apart by a predetermined distance 82. The probes are oriented longitudinally across a diameter of the mixing chamber 60 in a generally horizontal plane to make available a greater surface area for a beverage 11 to contact. In one embodiment, the conductivity probes 80 are inserted through apertures 84 in the mixing chamber 60. In one embodiment, the probes are press fit into the apertures 84. The press fit is achieved by sizing the apertures 84 to be slightly smaller than the corresponding dimension of the probes 80. When the body 61 of the spout 62 is formed of a plastic material and the probe is formed of a material which generally is harder than the material used to form the body 61. Insertion of the probes into the apertures 84 will tend to force the probe 80 into the material providing a tight fit between the probes and apertures 84. The tight fit prevents leakage of liquid through the apertures 84 along the probe 80.

It is also contemplated that other orientations and numbers of the conductivity probes 80 may be used. For example, conductivity probes 80 may be integrally molded or "in-molded" into the sides of the mixing chamber 61. In this orientation, the conductivity probes 80 will form two discrete portions of the interior surface of the mixing chamber 60. These discrete portions may lie within the same plane or in a non-planar orientation.

In another orientation, conductivity probes 80 may be inserted through apertures 84 in the mixing chamber 60 and terminate at the inner surface of the mixing chamber 60, exposing only a terminal end of the conductivity probe 80. These conductivity probes 80 may be disposed on opposite sides of the mixing chamber 60, proximate to one another, in a different planar orientation, vertically oriented, angularly oriented, or in any other orientation which those of skill in the art may find practical. In any orientation, conductivity probes 80 are provided in the interior of the mixing chamber 60 for measuring the conductivity of a beverage 11 which pools therein. It is also contemplated that photometric sensors may be used instead of conductivity probes 80 to detect the relative amount of beverage concentrate 14 within a beverage 11 in the mixing chamber 60. The components including the probes 80 connected to the controller 100 and lines 103*a*, 103*b* comprise one form of means for detecting conductivity 304 or a conductivity detector.

The conductivity probes 80 are coupled over a line 103 to controller 100. The conductivity probes 80 are electrodes which are spaced apart a predetermined distance. The conductivity probes 80 are electrically insulated from one another in their attachment to the body 61 through the use of an insulating material or insulating jacket on the probes so as to allow the conductivity probes 80 to accurately measure without interference from the material forming the mixing chamber 60. The probes 80 are conductive within the chamber 60 with the liquid in the chamber 60 forming a path conductively coupling the probes 80 in the chamber 60. The conductivity probes 80 provide measurements of the electrical conductivity of the beverage 11 contained in an area in which the probes lie, generally between the conductivity probes 80. The measurements are taken at preprogrammed time intervals throughout the time period a beverage 11 is being dispensed, thus allowing real time feedback to the controller 100.

The measurements are taken by passing a known electrical current through 103*a*, coupled to the controller 100, a first of two conductivity probes 80 into a beverage 11 contained within the lower portion 70 of mixing chamber 60. The electrical current received at a second conductivity probe 80 is detected by the controller 100, over line 103*b*, and measured to derive a conductivity measurement of the beverage 11. The measurement of electrical current that is detected by the second conductivity probe 80 is communicated over line 103*b* to controller 100 in real time as the beverage concentrate 14 and diluting water 18 are dispensed through inlet tube 24 into the mixing chamber 60.

Controller 100 interprets the real time conductivity measurements by comparing them against a preprogrammed or user selected target conductivity reading or range of readings. If the real time conductivity measurements of the conductivity probes 80 fall within the preprogrammed range of conductivity readings, the beverage being produced is deemed to be within the desired range and the controller 100 will continue to operate the pump 20 at its current speed or otherwise deliver concentrate at a desired rate.

If the real time conductivity measurements are outside of the preprogrammed range of conductivity readings, the beverage 11 being produced is deemed to be outside the desired range. In this case, the controller 100 will either increase or decrease the rate of pump 20 dependant on whether the real time conductivity measurements fall below or above the preprogrammed range of conductivity readings.

As the speed of pump 20 is adjusted by controller 100, the volume of beverage concentrate 14 is either increased or decreased to bring the subsequent real time conductivity measurements within the preprogrammed range of conductivity readings. The resulting beverage that enters the mixing chamber 60 is then measured by the conductivity probes 80 and communicated to controller 100 which again compares the real time conductivity measurements to the preprogrammed range of conductivity readings and either maintains the speed of pump 20 or adjusts the speed again to bring the real time conductivity measurements within the preprogrammed range of conductivity readings.

While it is contemplated that the controller may adjust both the speed of pump 20 and the relative position of controllable valve 36 and flow restrictor 44, in one embodiment the pump 20 is an example of the primary means for controlling the concentration of beverage concentrate 14 in the beverage 11, and thus the conductivity. In one embodiment, the pump 20 is a peristaltic pump. The controller 100 can slightly increase or decrease the speed of a peristaltic pump based on readings of the conductivity probes 80 in order to precisely increase or decrease the volume of beverage concentrate 14 being dispensed. While a peristaltic pump is disclosed, other pumps and means for controllably delivering concentrate are contemplated which will serve the same function.

By interpreting and responding to changes in the real time conductivity data being gathered by the conductivity probes 80, the controller 100 can adapt to any fluctuations in the conductivity of the beverage 11 being dispensed and ensure that the beverage 11 being dispensed is more uniform and falls within a more precise range.

An additional feature which the present disclosure provides is the ability to monitor when the container 16 has generally exhausted the supply of beverage concentrate 14. The conductivity probes 80 may detect a change in conductivity of the beverage 11 produced after appropriate adjustments in pump 20 speed have been made. Such measurements may then be communicated to controller 100 over line 103. The controller 100 may respond to the conductivity measurements if they are outside a preprogrammed range by locking out the beverage dispensing system or indicating that the container 16 is empty on the control panel 50. For example, if the conductivity probes 80 detect a decrease or increase in conductivity of greater than 50%, the controller may be preprogrammed to lockout the beverage dispensing system 10 and indicate that the container 16 holding beverage concentrate 14 is empty.

While preferred embodiments have been illustrated and described in detail in the drawings and foregoing description, such illustrations and descriptions are considered to be exemplary and not restrictive in character, it being understood that only illustrative embodiments have been shown and described and that all changes and modifications that come within the spirit of the invention are desired to be protected. There are a plurality of advantages of the present disclosure arising from various features set forth in the description. It will be noted that alternative embodiments of the disclosure may not include all of the features described yet still benefit from at least some of the advantages of such features. Those of ordinary skill in the art may readily devise their own implementations of the disclosure and associated methods that incorporate one or more of the features of the disclosure and fall within the spirit and scope of the present disclosure as defined by the appended claims.

The invention claimed is:

1. A beverage producing apparatus for controllably combining a concentrate and a dilution material to produce a beverage, the beverage producing apparatus comprising:
   means for delivering concentrate;
   means for delivering dilution material;
   a controller operatively coupled to and operatively controlling the concentrate delivering means and the dilution material delivering means;
   means for detecting conductivity;
   a mixing chamber for combining the concentrate and the dilution material;
   orienting at least two conductivity probes in a horizontally spaced apart orientation in the mixing chamber for detecting conductivity at a horizontal location in the mixing chamber; and
   the conductivity means being operatively coupled to the controller for providing conductivity information relating at least a mixture of the concentrate and dilution material, the controller operatively controlling the dispensing of concentrate and dilution material to maintain the conductivity of the mixture in a desired conductivity range.

2. A method for controlling dispensing of a beverage, the method comprising the steps of:
   providing means for delivering concentrate;
   providing means for delivering dilution material;
   providing a controller operatively coupled to the concentrate delivering means and the dilution material delivering means;
   providing a mixing chamber for receiving the concentrate and the dilution material;
   providing means for detecting conductivity;
   positioning the conductivity detecting means in a horizontal orientation in the mixing chamber;
   initiating dispensing of a beverage by sending a signal to the controller;
   controllably dispensing the dilution material from the dilution material delivering means to the mixing chamber;
   dispensing the concentrate from the concentrate delivering means to the mixing chamber;
   mixing the concentrate and dilution material in the mixing chamber to produce the beverage;
   pooling the concentrate and dilution material prior to dispensing in an area proximate to at least a portion of the conductivity detecting means;
   detecting the conductivity of the beverage at a horizontal location in the mixing chamber prior to dispensing; and
   controllably adjusting at least one of the concentrate and dilution material when the conductivity is not at least one of a predetermined level and range.

3. A system for controllably dispensing beverages and maintaining a beverage dispensed thereby within a desired conductivity range, the system comprising:
   means for delivering concentrate;
   means for delivering dilution material;
   a controller operatively coupled to and operatively controlling the concentrate delivering means and the dilution material delivering means;
   a mixing chamber for receiving and combining the concentrate and the dilution material;
   means for detecting conductivity including at least two conductive probes;
   orienting the at least two conductive probes in a horizontally spaced apart orientation in the mixing chamber for detecting conductivity at a horizontal location in the mixing chamber; and
   the conductivity means being operatively coupled to the controller for providing conductivity information relating to at least a mixture of the concentrate and dilution material, the controller operatively controlling the dispensing of the concentrate and dilution material to maintain the conductivity of the mixture in a desired conductivity range.

4. A beverage producing apparatus for controllably combining a concentrate and a dilution material to produce a beverage, the beverage producing apparatus comprising:

a controllable concentrate dispensing assembly;

a controllable dilution material dispensing assembly;

a mixing chamber for receiving and combining the concentrate and dilution material;

a controller operatively coupled to and operatively controlling the concentrate dispensing assembly and the dilution material dispensing assembly;

a conductivity detector including at least two conductive probes;

orienting the at least two conductive probes in a horizontally spaced apart orientation in the mixing chamber for detecting conductivity at a horizontal location in the mixing chamber; and the conductivity detector being operatively coupled to the controller for providing conductivity information relating at least a mixture of the concentrate and dilution material, the controller operatively controlling the dispensing of concentrate and dilution material to maintain the conductivity of the mixture within at least one of a predetermined conductivity level and a predetermined conductivity range.

5. A method for controlling dispensing of a beverage, the method comprising the steps of:

providing a controllable concentrate dispensing assembly;

providing a controllable dilution material dispensing assembly;

providing a controller operatively connected to the concentrate dispensing assembly and the dilution material dispensing assembly;

providing a mixing chamber for receiving the concentrate and the dilution material;

providing a conductivity detector;

positioning the conductivity detecting means in a horizontal orientation in the mixing chamber;

initiating dispensing of a beverage by sending a signal to the controller;

controllably dispensing the dilution material from the dilution material delivering means to the mixing chamber;

dispensing the concentrate from the concentrate delivering means to the mixing chamber;

mixing the concentrate and dilution material in the mixing chamber to produce the beverage;

pooling the concentrate and dilution material prior to dispensing in an area proximate to at least a portion of the conductivity detecting means;

detecting the conductivity of the beverage at a horizontal location in the mixing chamber prior to dispensing; and controllably adjusting at least one of the concentrate and dilution material when the conductivity is not at least one of a predetermined level and range.

6. A system for controllably dispensing beverages and maintaining a beverage dispensed thereby within a desired conductivity range, the system comprising:

means for delivering concentrate;

means for delivering dilution material;

a mixing chamber for receiving and combining the concentrate and the dilution material;

a controller operatively coupled to and operatively controlling the concentrate delivering means and the dilution material delivering means;

means for detecting conductivity including at least two conductive probes;

orienting the at least two conductive probes in a horizontally spaced apart orientation in the mixing chamber for detecting conductivity at a horizontal location in the mixing chamber; and the conductivity means being operatively coupled to the controller for providing conductivity information relating to at least a mixture of the concentrate and dilution material, the controller operatively controlling the dispensing of the concentrate and dilution material to maintain the conductivity of the mixture in a desired conductivity range.

* * * * *